United States Patent
Hake et al.

[11] Patent Number: 5,843,041
[45] Date of Patent: Dec. 1, 1998

[54] HYPODERMIC NEEDLE GUARD AND METHOD TO PREVENT NEEDLE STICK INJURIES

[76] Inventors: Lawrence W. Hake, 3493 W. Guenther Rd.; Michael R. Flodman, 3981 Reuting Rd., both of Grand Island, Nebr. 68803

[21] Appl. No.: 771,173

[22] Filed: Dec. 20, 1996

Related U.S. Application Data

[63] Continuation of Ser. No. 630,171, Apr. 10, 1996, abandoned, which is a continuation of Ser. No. 247,858, May 23, 1994, abandoned, which is a continuation of Ser. No. 52,259, Apr. 23, 1993, Pat. No. 5,314,414, which is a continuation-in-part of Ser. No. 704,359, May 23, 1991, Pat. No. 5,256,153, which is a continuation-in-part of Ser. No. 317,733, Mar. 2, 1989, Pat. No. 5,019,051.

[51] Int. Cl.⁶ ..................................................... A61M 5/32
[52] U.S. Cl. ............................................................ 604/198
[58] Field of Search .................................... 604/192, 197, 604/198, 263, 110

[56] References Cited

U.S. PATENT DOCUMENTS

| | | | |
|---|---|---|---|
| 4,425,120 | 1/1984 | Sampson | 604/198 |
| 4,631,057 | 12/1986 | Mitchell | 604/198 |
| 4,654,034 | 3/1987 | Masters et al. | 604/192 |
| 4,659,330 | 4/1987 | Nelson et al. | 604/192 |
| 4,664,653 | 5/1987 | Sagstetter et al. | 604/197 |
| 4,664,654 | 5/1987 | Strauss | 604/198 |
| 4,666,435 | 5/1987 | Braginetz | 604/198 |
| 4,668,223 | 5/1987 | Grotehuis | 604/191 |
| 4,681,567 | 7/1987 | Masters | 604/198 |
| 4,693,708 | 9/1987 | Wanderer | 604/198 |
| 4,695,274 | 9/1987 | Fox | 604/198 |
| 4,702,738 | 10/1987 | Spencer | 604/198 |
| 4,710,170 | 12/1987 | Haber et al. | 604/110 |
| 4,723,943 | 2/1988 | Spencer | 604/198 |
| 4,731,059 | 3/1988 | Wanderer et al. | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,758,231 | 7/1988 | Haber et al. | 604/198 |
| 4,762,516 | 8/1988 | Luther | 604/164 |
| 4,772,272 | 9/1988 | McFarland | 604/198 |
| 4,778,453 | 10/1988 | Lopez | 604/110 |
| 4,801,295 | 1/1989 | Spencer | 604/198 |
| 4,816,022 | 3/1989 | Poncy | 604/198 |
| 4,816,024 | 3/1989 | Sitar et al. | 604/192 |
| 4,846,796 | 7/1989 | Carrell | 604/110 |
| 4,850,994 | 7/1989 | Zerbst et al. | 604/198 |
| 4,874,383 | 10/1989 | McNaughton | 604/198 |
| 4,927,417 | 5/1990 | Moncada | 604/198 |
| 4,976,702 | 12/1990 | Andrews et al. | 604/198 |
| 5,045,066 | 9/1991 | Scheuble et al. | 604/198 |
| 5,088,988 | 2/1992 | Talonn et al. | 604/198 |
| 5,106,380 | 4/1992 | Lobello | 604/198 |
| 5,127,910 | 7/1992 | Talonn et al. | 604/198 |
| 5,147,326 | 9/1992 | Talonn et al. | 604/198 |
| 5,156,599 | 10/1992 | Ranford | 604/198 |
| 5,160,326 | 11/1992 | Talonn et al. | 604/198 |
| 5,169,392 | 12/1992 | Ranford | 604/198 |
| 5,197,953 | 3/1993 | Colonna | 604/198 |
| 5,273,543 | 12/1993 | Bell et al. | 604/110 |

FOREIGN PATENT DOCUMENTS

| | | | |
|---|---|---|---|
| 350186 | 10/1990 | European Pat. Off. | A61M 5/32 |
| 3842107 | 12/1988 | Germany | A61M 5/32 |
| 9004984 | 5/1990 | WIPO | A61M 5/00 |

*Primary Examiner*—Ronald Stright, Jr.
*Assistant Examiner*—Cris L. Rodriguez
*Attorney, Agent, or Firm*—Banner & Witcoff Ltd

[57] ABSTRACT

A needle guard and a method to prevent needle stick injuries are disclosed, for use with a hypodermic syringe or other instrument with a sharp point. The needle guard, comprises a protective sleeve with a fitting, that may be used with or added to a syringe and needle assembly. The interior of the fitting contains an annular core adapted to permanently engage the fitting on the syringe barrel. Radial arms extending from the core align and cooperate with the slidable sleeve. Prior to and during use of the needle, the sleeve remains in a retracted position covering the barrel of the syringe. After the needle has been used, the sleeve is pushed forward into its locked extended position, so that the end of the sleeve extends beyond the tip of the needle. The tip of the needle is thereby shielded, preventing accidental sticks.

13 Claims, 8 Drawing Sheets

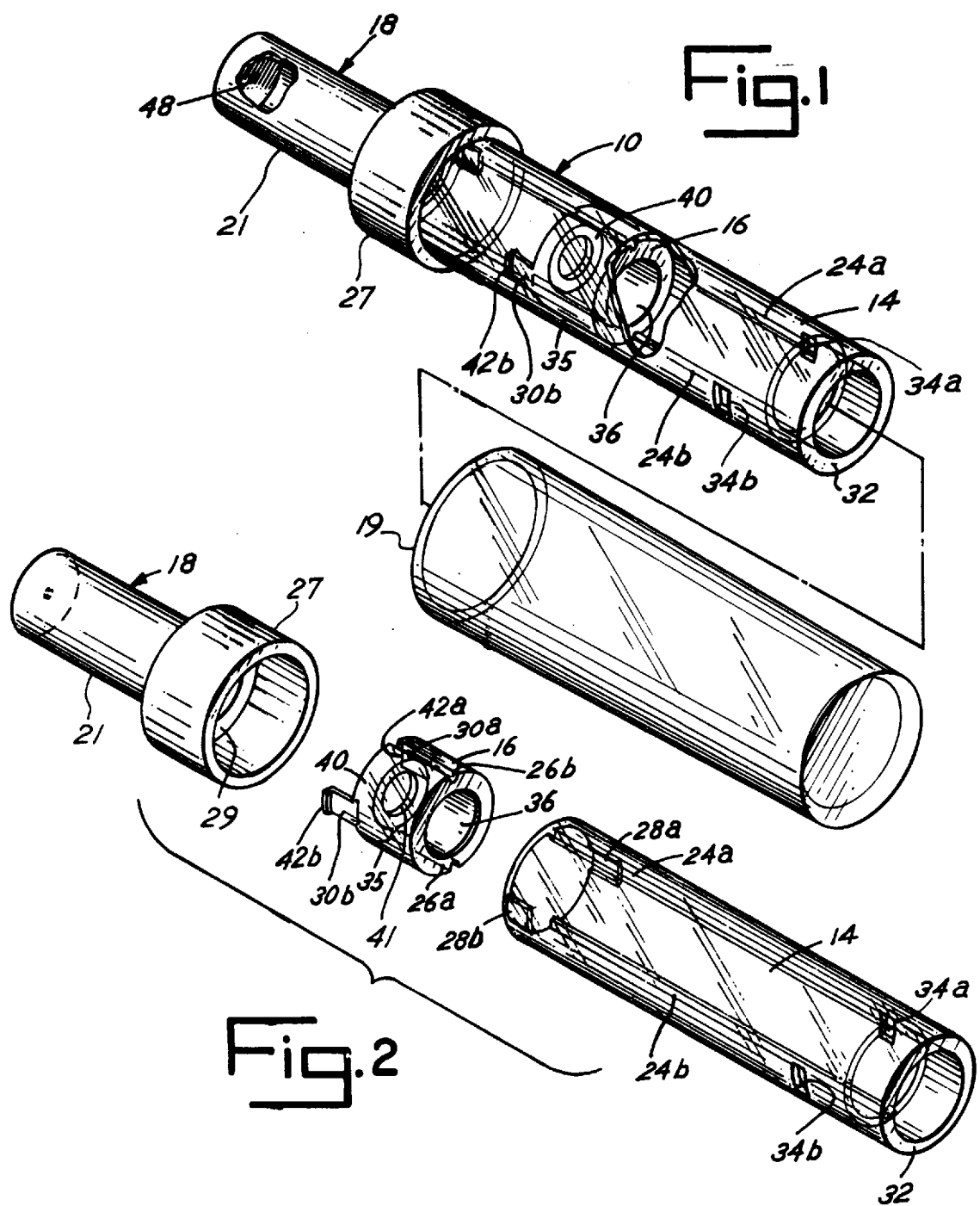

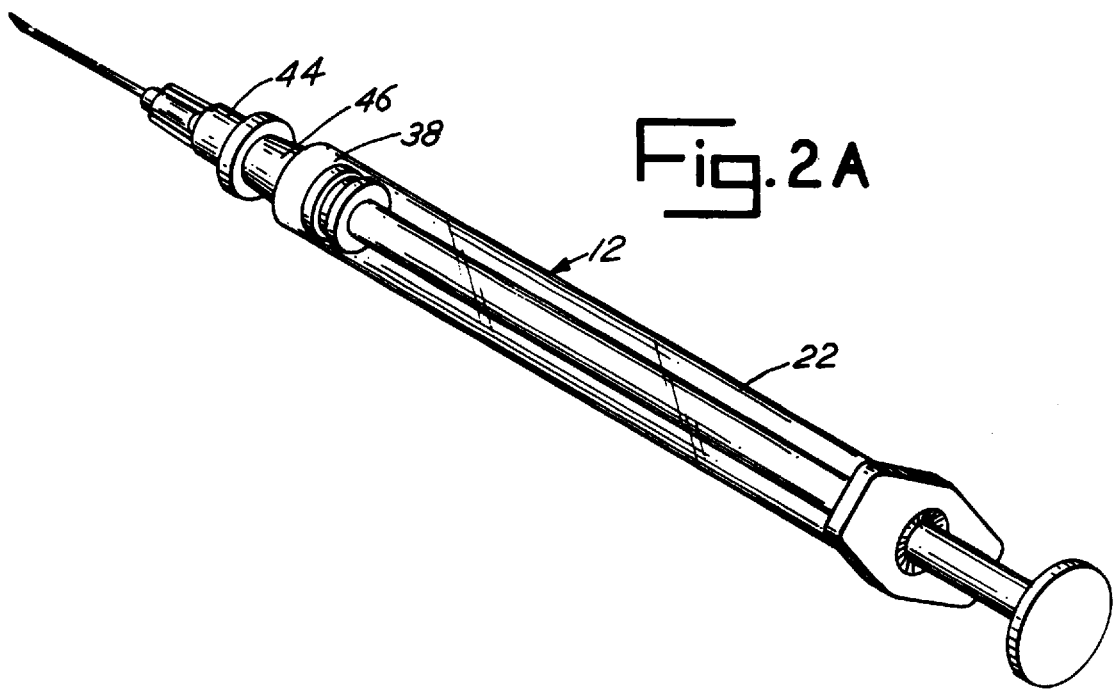
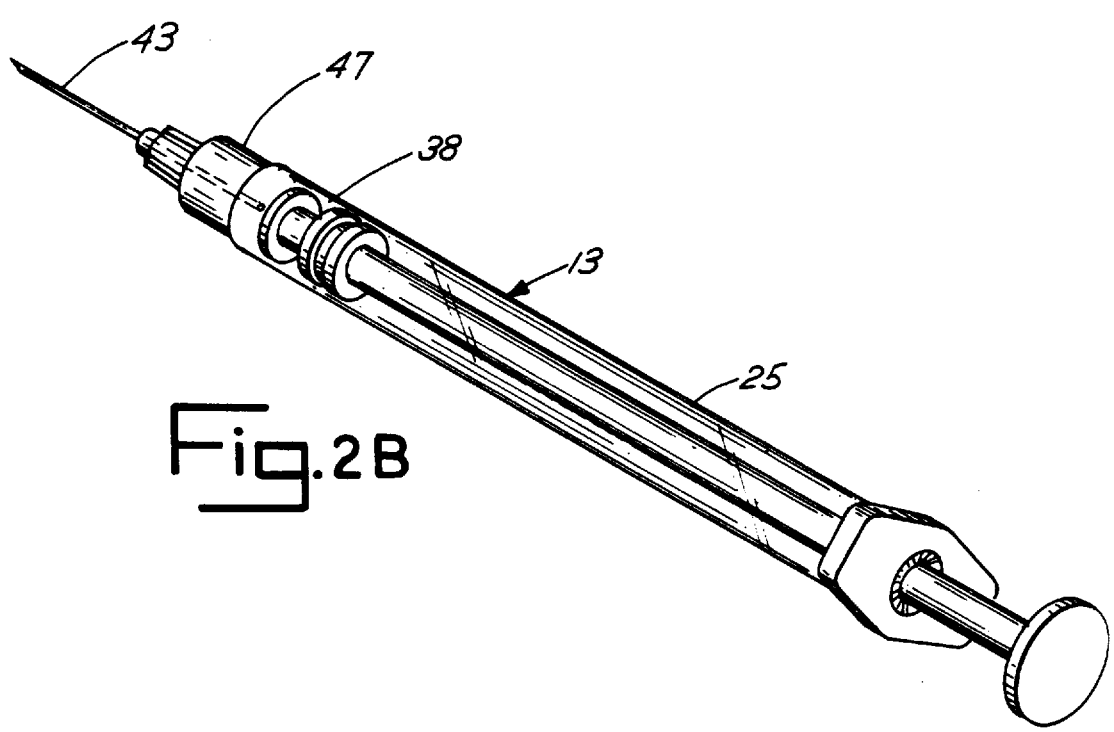

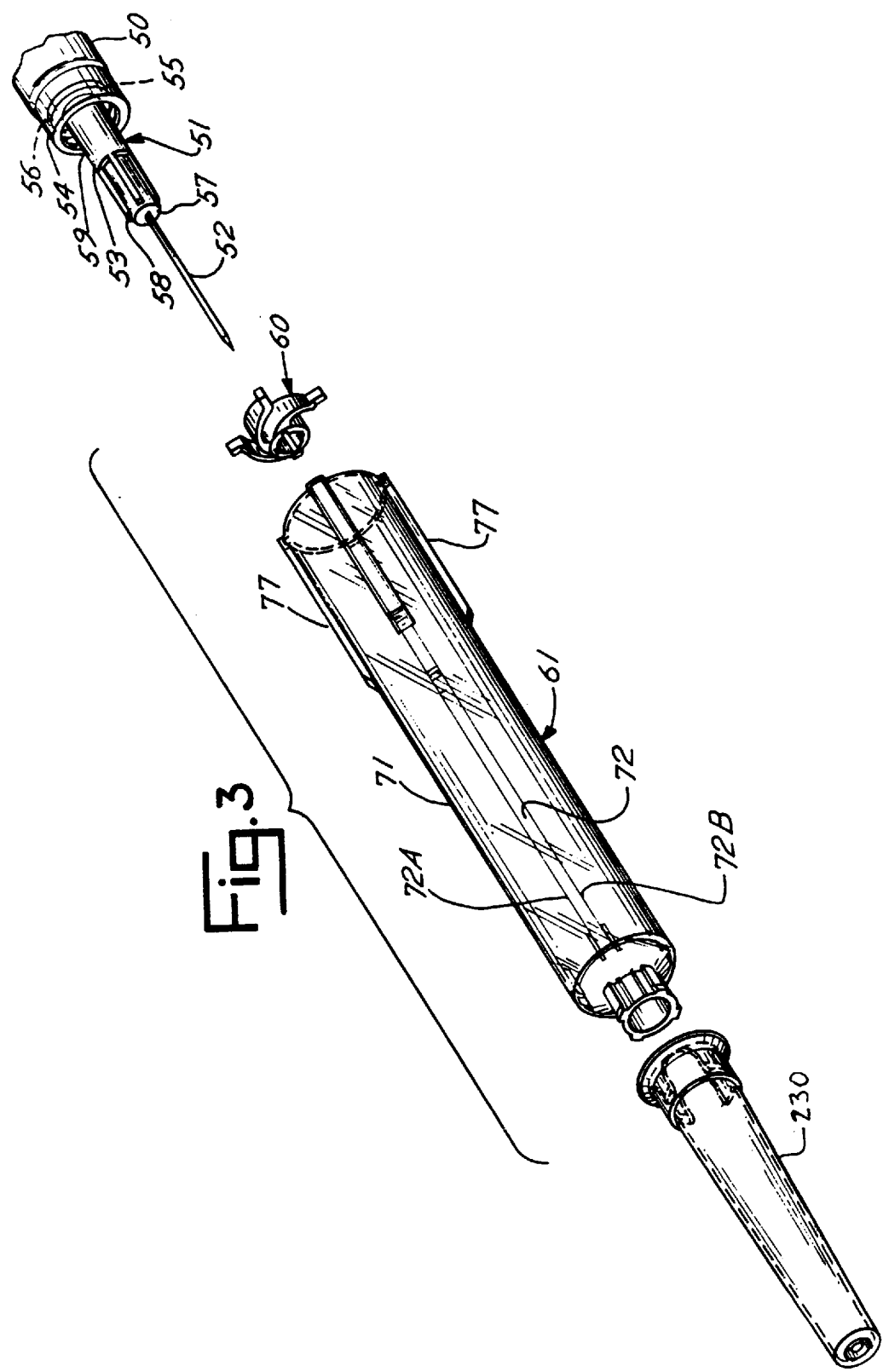

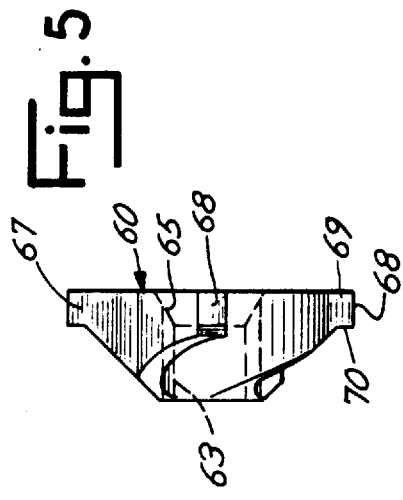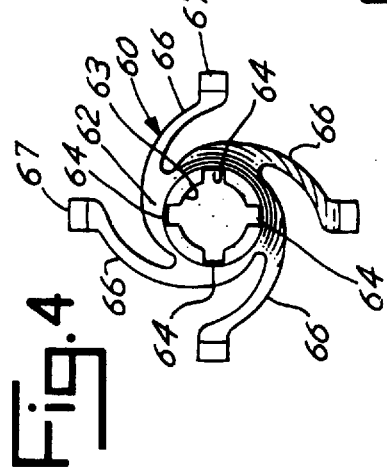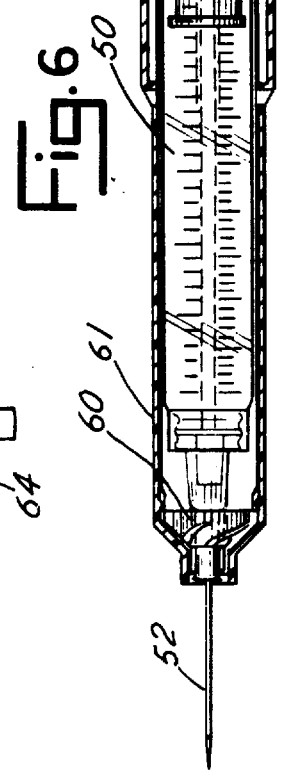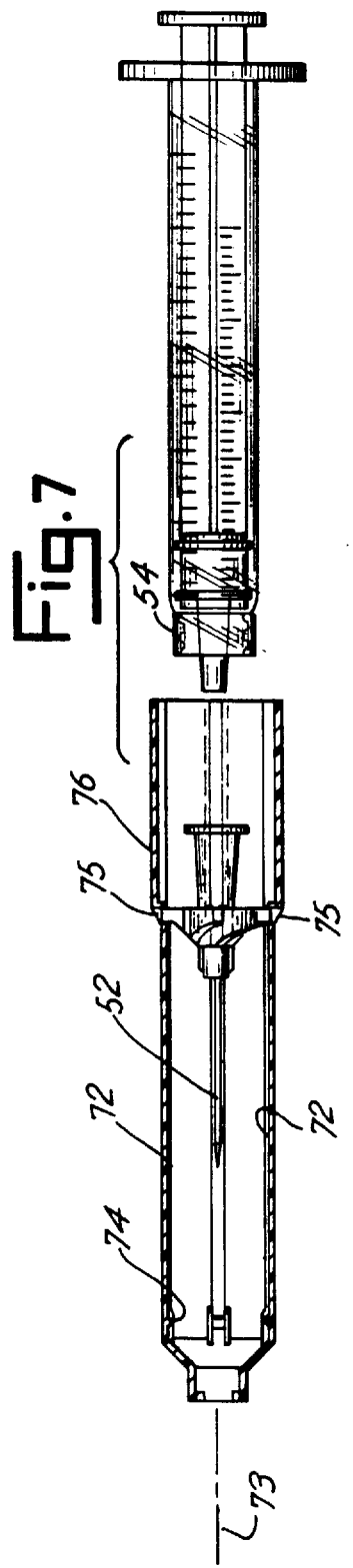

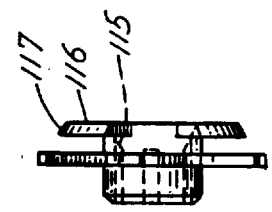
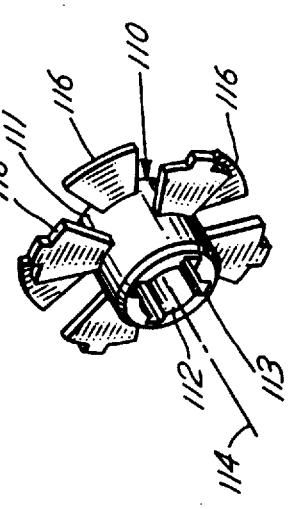
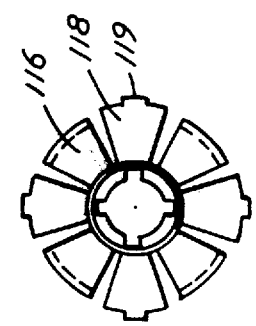
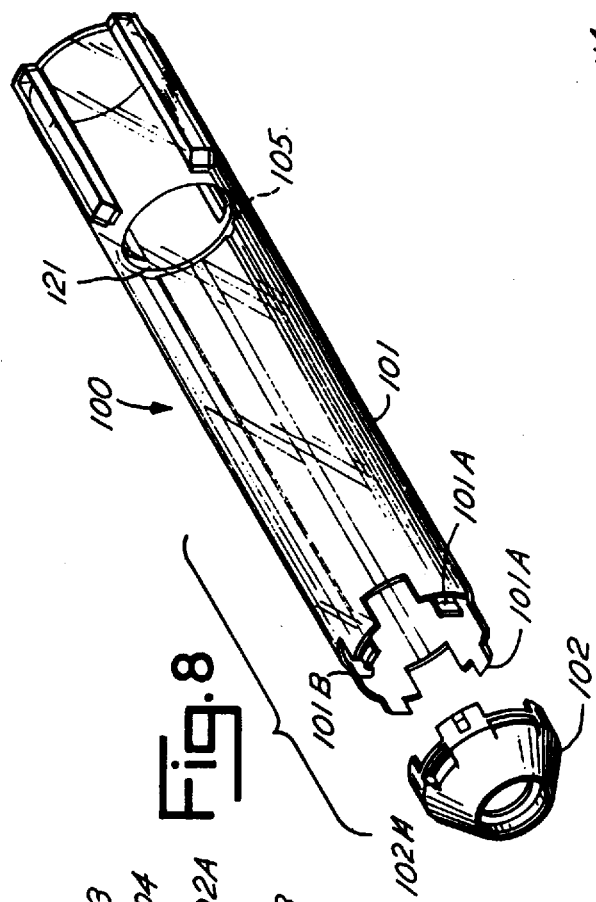
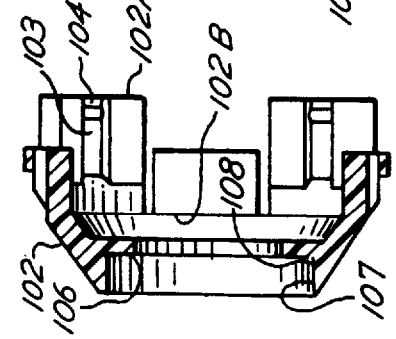
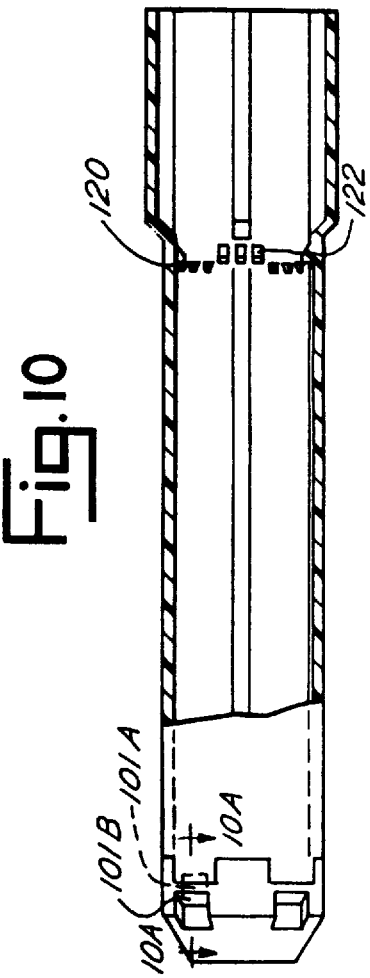

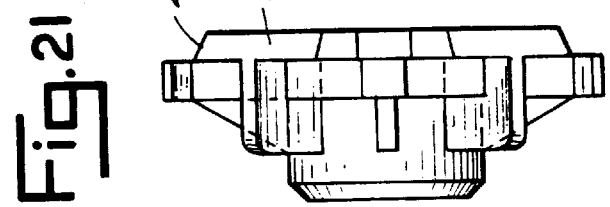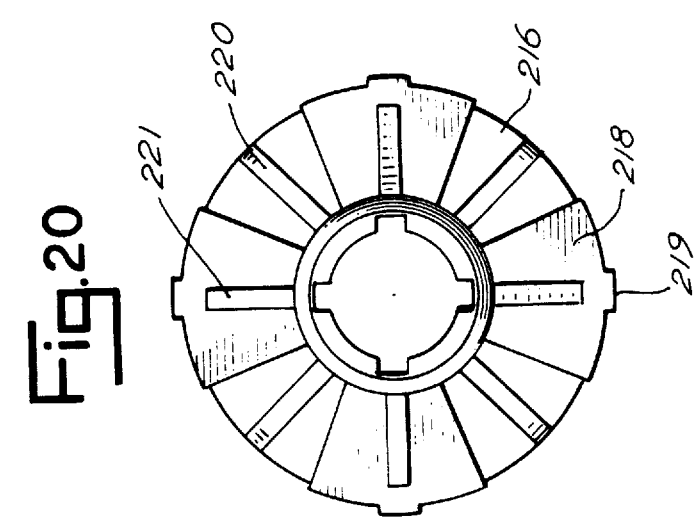

HYPODERMIC NEEDLE GUARD AND METHOD TO PREVENT NEEDLE STICK INJURIES

This is a continuation of application Ser. No. 08/630,171, filed Apr. 10, 1996, now abandoned which itself is a continuation of application Ser. No. 08/247,858, filed May 23, 1994, now abandoned which itself is a continuation application of Ser. No. 08/052,259, filed Apr. 23, 1993, now U.S. Pat. No. 5,314,414, which itself is a continuation-in-part of application Ser. No. 07/704,359, filed May 23, 1991, now U.S. Pat. No. 5,256,153, which itself a continuation-in-part of application Ser. No. 07/317,733, filed Mar. 2, 1989, now U.S. Pat. No. 5,019,051.

BACKGROUND OF THE INVENTION

This invention relates to syringes, and more particularly to a syringe construction designed for the prevention of needle-stick injuries.

Hypodermic syringes are widely used to inject substances into and to draw samples from living subjects, such as human beings, animals, and from inanimate items. A hypodermic syringe typically includes a barrel that contains the substance to be injected or that is available to receive the sample to be drawn, and a needle which is connected to the interior of the barrel and projects from an end of the barrel. A plunger is reciprocal in the barrel to effect movement of the substance. Hypodermic syringes may be either reusable or disposable. Those that are disposable are normally discarded after use to avoid spread of contamination or disease.

It has been observed that there is a low but ever-present rate of needle-stick injuries suffered by syringe users such as medical practitioners after a syringe has been used. In one study of needle-stick injuries, disposable syringes were involved in 6.9 needle-stick injuries per 100,000 items purchased, and accounted for 35 percent of the total number of needle-stick injuries from all sources. See Rates of Needle-Stick Injury Caused By Various Devices In A University Hospital, J. Jagger, M.P.H., Ph.D., E. H. Hunt, R.N., J. Brand-Elnaggar, B.A., & R. D. Pearson, M.D., 319 *New England Journal or Medicine* 284–288, Aug. 4, 1988. The most common mechanism of needle-stick injury from disposable syringes was due to attempts by hospital personnel to place a cap over the needle after use of the syringe, usually to protect themselves or others from the contaminated needle. The study concluded that efforts to implement safety guidelines have been ineffective and are unlikely to eliminate such injuries in the future. The study recommended redesign of instruments to eliminate use of needles, provision of some sort of fixed barrier between the user and the needle, or allowing the user's hands to remain behind the needle as it is covered.

Concern for the safety of health care workers has become acute in recent years, particularly due to the spread of the acquired immunodeficiency syndrome (AIDS). Indeed, needle-sticks by contaminated syringes have been attributed as a cause of such infection in health care workers. Although an initial needle-stick injury may appear minor, the possibility of infection is serious enough to warrant efforts to entirely eliminate the possibility of a needle-stick injury.

A wide variety of hypodermic syringes have been proposed in an attempt to prevent needle-stick injuries. These structures generally require modification of the syringe barrel. For example, U.S. Pat. No. 4,737,144 to Choksi discloses a syringe with a sleeve which can be locked in a retracted position and also an extended position. The locking mechanism includes a slot formed near the end of the barrel which cooperates with spring urged tabs on the sleeve.

U.S. Pat. No. 4,425,120 to Sampson, et al., discloses a needle guard mounted on the barrel of the syringe. The guard can be releasably locked in the retracted position or locked in the extended position. Locking of the guard is effected by a track on the internal surface of the guard and track-engaging members on the barrel.

U.S. Pat. No. 4,573,976, also to Sampson, et al., discloses a similar structure with different locking means U.S. Pat. No. 4,356,822 to Winstead-Hall discloses a syringe assembly having a barrel and tubular guard with multiple locking members provided for securing the barrel and cap in a number of relative axial positions. A frangible end closure may be provided on the end of the cap closest to the needle. The locking members permit different locked positions for exposing different amounts of the needle.

Another approach is to provide a shield integral with the needle instead of the barrel. U.S. Pat. No. 3,134,380 to Armano discloses a collapsible needle guard integral with the needle portion of the syringe. The needle with guard is assembled and sterilized by the manufacturer. The purpose of the guard is to shield the needle from the view of the patient.

None of these structures are known to be in widespread use. Most standard hypodermic syringe assemblies presently in use are unshielded and do not resolve the problem of needle sticks.

SUMMARY OF THE INVENTION

Briefly, the present invention comprises an improved needle guard that is compatible with a typical, unguarded hypodermic syringe, for example, a syringe with a permanently mounted needle. The invention also comprises a method to prevent needle stick injuries. The needle guard is simple to use, inexpensive, does not require modification of the typical, prior art syringe and is effective to prevent needle-stick injuries. The needle guard is effected by placement of an irreversible fixed barrier over the needle after use. The hands of the syringe user remain behind the needle point as the barrier is moved into position over the needle.

The needle guard includes a special fitting or bushing cooperative with the syringe needle hub and a protective sleeve which is slidable on the barrel of the syringe between a position which reveals the needle and a position which covers the needle. The sleeve engages the hub fitting to lock the sleeve over the needle in the protective position covering the needle. A packaging cap and packaging body may also be provided as optional features.

The special fitting or bushing which fits on the needle hub and coacts with the sleeve has various preferred forms. It mounts on the needle hub of the syringe unit by cutting into and deforming the needle hub of the syringe. The fitting is thus positioned to guide and lock the slidable protective sleeve over the needle.

In one method of assembling the needle guard onto the syringe, the fitting is placed inside the sleeve, and a packaging cap is placed on one end of the protective sleeve. The user grasps the needle guard sleeve and orients the needle guard sleeve so that the open end of the protective sleeve faces the user. The user then slides the needle and syringe barrel into the open end of the protective sleeve, while simultaneously holding the packaging cap on the other end of the sleeve. The needle is then directed into the packaging cap so that the needle hub of the syringe will contact and grip onto the fitting. The needle hub portion of the syringe thus deformably engages with the fitting or bushing contained within the sleeve and will project through the fitting so that the needle will extend into the protective packaging cap. The protected needle of the syringe is then ready for use but only after the packaging cap is removed so the hypodermic syringe is fully assembled with the needle guard sleeve in the retracted position.

After the syringe is used, the protective sleeve may be moved forward along the barrel in the direction of the needle point. The sleeve is pushed forward until the bushing and sleeve irreversibly lock. The sleeve of the needle guard now extends beyond the pointed tip of hypodermic needle preventing access to the needle and thus preventing a needle stick by the needle. Note, very importantly that the user of the syringe must operate or push the sleeve from a position behind the needle point thereby avoiding exposure of the operator's hand to a needle stick when moving the sleeve forward over the needle. Similarly, the protective cap is removed by withdrawing it from the needle in a manner which requires the operator to remove the cap in a direction moving away from the needle point.

Alternative designs for the bushing or fitting as well as the sliding sleeve and protective cap are described. These designs enhance the described operations of the component parts and the combination of elements. Accordingly, an object of the invention is to provide an improved construction for use in combination with needles and which prevents needle-stick injuries.

Another object of the invention is to provide such an improved construction which is both safe and effective.

Yet another object of the invention is to provide a needle guard that is inexpensive, easily manufactured, and is useful with existing needle constructions.

An advantage of this invention is its provision of a simple needle guard construction for use with syringes having permanently mounted needles and also for use with syringes of the type wherein the needle and hub are separable from the syringe barrel.

A further advantage of this invention is its provision of a simple method for preventing needle stick injuries.

Another advantage of the invention is its provision of a construction which is useful with standardized needles incorporated in various devices or mechanisms such as with a syringe unit, an intravenous set, an arterial blood gas syringe, and other such devices utilizing needles.

Other objects and advantages of the invention will become apparent from the following description of the invention.

BRIEF DESCRIPTION OF THE DRAWING

In the detailed description which follows, reference will be made to the drawing comprised of the following figures:

FIG. 1 is a perspective view of a first embodiment of the present invention, showing the needle guard with a packaging cap and packaging body;

FIG. 2 is an exploded isometric view of the embodiment of FIG. 1 showing the packaging cap, bushing, and a sleeve;

FIG. 2A is a perspective view of a standard hypodermic syringe with a removable needle;

FIG. 2B is a perspective view of a standard hypodermic syringe with a permanently mounted needle;

FIG. 3 is an exploded isometric view of an alternative embodiment of the invention depicting a sleeve which fits over the barrel of the syringe assembly as well as a fitting which fits over and engages the hub for the needle of the syringe assembly and a special cap that cannot be reattached after initial removal from the sleeve;

FIG. 4 is an enlarged front plan view of the fitting depicted in FIG. 3;

FIG. 5 is a side plan view of the fitting of FIG. 4;

FIG. 6 is a side cross sectional view of the fitting of the FIGS. 4 and 5 as incorporated in a syringe assembly and further depicts the protective sleeve in the retracted or unlocked position;

FIG. 7 is a partially exploded side sectional view illustrating a syringe assembly as well as the improved sleeve and fitting as positioned cooperatively with a needle and hub in an irreversibly locked position;

FIG. 8 is an exploded isometric view illustrating another embodiment of the sleeve and tapered end cap which fits over a barrel of a syringe assembly;

FIG. 9 is an enlarged side sectional view of a cap for the sleeve depicted in FIG. 8;

FIG. 10 is a side cross sectional view of the sleeve and cap shown in FIG. 8;

FIG. 11 depicts in an isometric view an alternative fitting designed for cooperation with the sleeve of FIG. 8 and the needle hub of a syringe assembly;

FIG. 12 is a front elevation of a fitting of Figure 11;

FIG. 13 is a side elevation of a fitting of FIG. 11;

FIG. 20 is a front elevation of a further alternative fitting;

FIG. 21 is a side elevation of a fitting of FIG. 20; and

FIG. 22 is an isometric view of a fitting of FIG. 20.

DESCRIPTION OF THE PREFERRED EMBODIMENTS

Figure 2D:
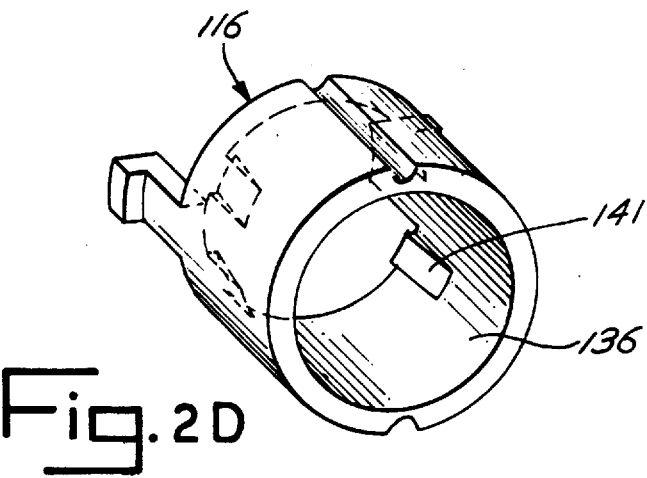
FIG. 2D is a perspective view of one embodiment of a bushing as utilized in the embodiment of FIG. 2C.

The present invention provides a unique construction and method to prevent needle-stick injuries resulting from use of currently available syringes. Some standard hypodermic syringes, such as syringe 12 of FIG. 2A, have detachable needles 44. For illustration purposes, syringe 12 is shown fully assembled in the ordinary fashion. Other commercially available hypodermic syringes, such as syringe 13 of FIG. 2B, have a unitary construction, so that the needle 43 is permanently mounted at the end of the barrel 25 of the syringe 13. The embodiment of the invention in FIGS. 1 and 2 may be used with the permanently mounted type of syringe 13 shown in FIG. 2B or a detachable mounted type of syringe as shown in FIG. 2A. The invention comprises an apparatus for combination with standard syringes commonly in use.

The needle guard 10 is comprised of a protective sleeve 14 and a fitting or bushing 16, as well as an optional packaging cap 18 and optional packaging body 19. The needle guard 10 is mounted on the syringe 13, used therewith, and then the assembly may be discarded. When the needle guard 10 is positioned upon the syringe 13, the bushing 16 deformably fits on the needle hub portion 47 of the barrel 25 of the syringe 13 and slidably retains the sleeve 14. Sleeve 14 is slidable between a retracted, needle exposed position and an irreversible extended needle protective or covered position.

The optional packaging cap 18 is comprised of a first portion 21 and a second portion 27, both portions being hollow and generally cylindrical in shape. First portion 21 is sealed at its top end by wall 48. The bottom end of first portion 21, opposite the top end, is open. Thus, first portion 21 defines a space in which a portion of a hypodermic needle may be disposed.

Referring to FIG. 2, the top end of second portion 27 is connected to the bottom end of first portion 21, thus defining an internal annular shoulder 29. First portion 21 and second portion 27 may be joined by means known in the art, or may be molded together as an integral unit. The bottom end of second portion 27, opposite the top end, is open, and defines a space that may slidably cooperate with the exterior surface of sleeve 14.

Referring again to FIG. 2, the protective sleeve 14 is a hollow, molded plastic cylindrical tube. In the alternative, the sleeve 14 might have another shape, with an oval or polygonal cross section, for example, so long as its interior cross section is adequate to admit the barrel 25 of the syringe 13 and is cooperative with the bushing 16. Sleeve 14 includes guide means keyed to the bushing 16. In FIGS. 1 and 2, the guide means comprise straight longitudinal ribs 24a and 24b on the interior surface of sleeve 14, which coact with grooves 26a and 26b on the exterior surface of bushing 16 to prevent rotation of the sleeve 14 relative to bushing 16.

Sleeve 14 also has means to limit axial movement of sleeve 14 relative to bushing 16, including two depressions or recesses 28a and 28b, located on the interior surface of sleeve 14 at its distal end near the packaging cap 18. Recesses 28a and 28b, spaced about 180° apart, are adapted to reversibly engage radially outwardly extending members of fitting 16 such as lugs or tangs 30a and 30b when the sleeve 14 is in the retracted, needle exposed position. Tangs 30a and 30b are biased radially outwardly, extend axially from the distal end of bushing 16 in the direction of the needle 43, and have the form of cantilever elastic members or beams. Tangs 30a and 30b terminate with radially outwardly extending lips or ridges 42a and 42b, respectively, that reversibly engage in recesses 28a and 28b or irreversibly engage with slots 34a and 34b in sleeve 14 as described below. Note, the recesses 28a, 28b serve to retain the lips 42a, 42b in a manner which does not apply stress or strain to the tangs 30a, 30b so that the tangs 30a, 30b will retain their elasticity. Lips 42a, 42b thus fit into the recesses 28a, 28b and the sides of the recesses 28a, 28b are sloped to permit the lips 42a, 42b to move out or be "cammed" out of the recesses upon application of axial force to the sleeve 14.

Means for irreversibly locking the needle guard 10 in the extended position are also provided on sleeve 14. As disclosed in FIGS. 1 and 2, such means comprise axial slots 34a and 34b located near the proximal end of sleeve 14, which are adapted to receive and irreversibly lock with the tangs 30a and 30b, and more particularly, the lips 42a and 42b of bushing 16. It has been found that axial orientation of the tangs 30a and 30b in the direction of the needle 43 (as shown in FIG. 2) provides superior locking force for limiting axial movement of the sleeve 14 in the direction opposite of the needle 43 when the sleeve is in the extended position. For limiting axial movement of sleeve 14 on the bushing 16 in the direction of the needle 43, sleeve 14 has a shoulder or an inwardly extending flange 32 at its proximal end. In this manner both the translational and rotational motion of the bushing 16 within the sleeve 14 is controlled during use of the hypodermic syringe 13 and needle guard 10.

The fitting or bushing 16 has a generally annular shape with an exterior cylindrical surface 35 adapted to slidably cooperate with the interior surface of sleeve 14. Fitting 16 has an interior cylindrical surface 36 adapted to slidably cooperate with the syringe barrel 25. Interior surface 36 of bushing 16 contains a deformable engagement means adapted to cooperatively mount bushing 16 in a fixed position on syringe barrel 25. In FIG. 2, the deformable engagement means is comprised of radially inwardly extending retaining flange 40 proximate the distal end of bushing 16. Flange 40 defines a sharp, interior annular tapered surface or edge 41, provided to prevent the barrel 25 from being pushed through the bushing 16 entirely, and, as described below, to engage the syringe. Retaining flange 40 is manufactured from a material that has a harder composition than the material composing needle hub 47 of syringe 13.

Bushing 16 preferably has two engageable members or tangs 30a, 30b, spaced about 180° from one another on the circumference of bushing 16 and cooperative with respective detention depressions 28a, 28b and slots 34a, 34b, on the inside of axially slidable sleeve 14. The lips 42a, 42b of tangs 30a and 30b thus reversibly engage depressions 28a and 28b of sleeve 14 when the sleeve 14 is in the retracted position to thereby hold sleeve 14 in place. When the sleeve 14 is slid in the direction of the needle 43 into the extended position, detent lips 42a, 42b irreversibly engage slots 34a, 34b spaced about 180° apart. Whether the lips 42a, 42b reversibly or irreversibly engage the sleeve 14 depends on the depth and shape of the engaging configuration of sleeve 14. Thus, slots 34a, 34b have a depth and shape that insures that lips 42a, 42b are fully and irreversibly engaged. Depressions 28a, 28b only partially engage lips 42a, 42b and this engagement can be overcome by a mild axial force.

The needle guard 10 may be provided as an "add-on" product, i.e., to be manually attached to a syringe separately obtained by the user. For assembly and packaging purposes, the bushing 16 will be slidably disposed within sleeve 14, by placement through the distal end of the sleeve 14 proximate the packaging cap 18. The distal portion of the sleeve-bushing combination slidably fits within the space defined by second portion 27 of packaging cap 18. Furthermore, as shown in FIG. 1, the assembled cap-sleeve-bushing unit slidably fits within packaging body 19 as an added measure of protection and cleanliness during shipment and use of the assembly. The generally cylindrical shape of packaging cap 18 cooperates with the generally conical shape of packaging body 19 to form a releasable, frictional fit between the cap 18 and the body 19.

To attach the needle guard onto the syringe, the user slidably removes the packaging body 19 from the needle guard assembly. With the packaging cap 18 still in place, the user slides syringe unit into the proximal end of sleeve 14 through the opening formed by shoulder 32 in protective sleeve 14. The needle hub portion 47 of syringe barrel 25 will eventually engage the retaining flange 40 of bushing 16. At this point, needle 43 will have passed through retaining flange 40 as needle hub 47 is pushed into contact with the interior edge 41 of flange 40. A portion of needle 43 will be disposed within packaging cap 18.

As can best be seen in FIG. 2, as the needle hub 47 of syringe barrel 25 engages the interior edge 41 of flange 40, the bushing 16 will be forced in the direction of the packaging cap 18. However, tangs 30a, 30b will abut interior shoulder 29 of packaging cap 18, providing a counter-force, opposite in direction to the movement of the syringe 25. This counter-force may be maintained when the user grasps the cap 18 with his or her other hand.

The movement of the syringe 25 now being stopped, continued application of force to the syringe 25 results in the interior edge 41 of flange 40 cutting into and penetrating the needle hub 47 of syringe barrel 25, due to the relative hardness of the flange 40 and syringe barrel 25 as noted above. The penetration of flange 40 into the surface of the needle hub 47 deformably and permanently affixes the bushing 16 to the needle hub 47 of syringe 13 (or needle hub 44 of syringe 12 in FIG. 2A).

In the preferred embodiment shown in FIG. 2D, the uniform annular retaining flange 40 is replaced with a series of sharp axial ridges 141 distributed about the circumference of the interior surface 136 of bushing 116, near the distal end of bushing 116. The ridges 141 are shaped generally as inclined planes, the ridges being inclined inwardly from the interior surface 136 in the radial direction. As with the uniform flange 40, the ridges 141 are manufactured from a material that is harder than the material from which the needle hub 47 is manufactured, thus allowing the ridges to penetrate and engage needle hub 47, as described above. In the preferred embodiment, the ridges 141 are made of an acrylic material, whereas the typical syringe barrel is made of polypropylene or polyethylene. The series of sharp ridges 141 has been found to be superior to the uniform flange 40, due to variations in the size of the needle hub 47 that occur during syringe manufacturing.

Figure 2C:
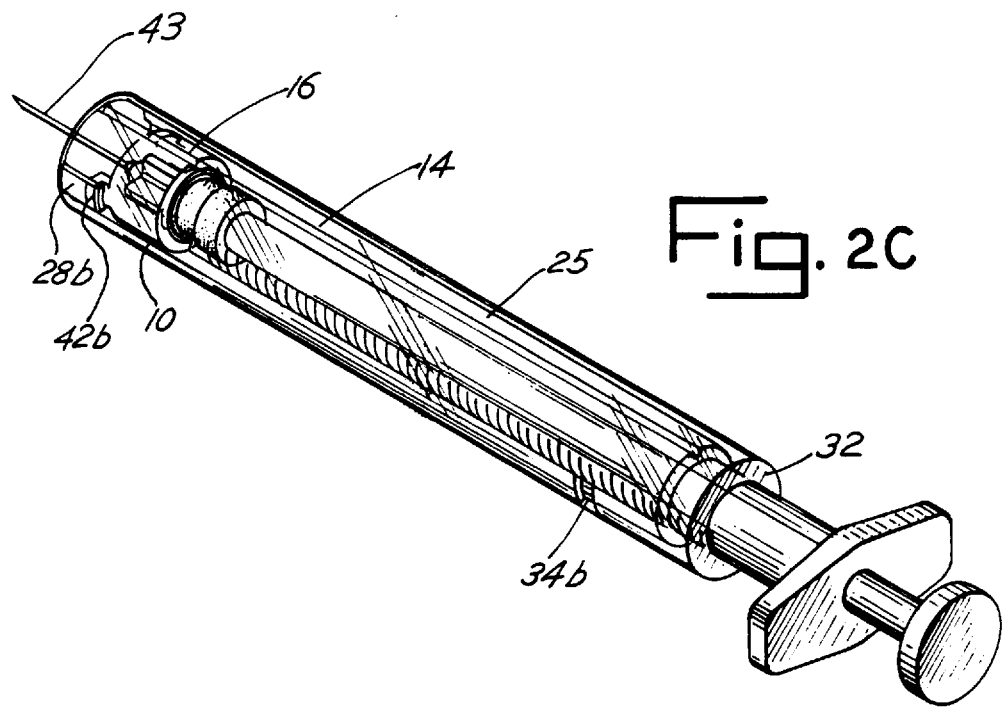
FIG. 2C is a perspective view of a needle guard mounted on a standard hypodermic syringe with a permanently mounted needle.
Figure 14:
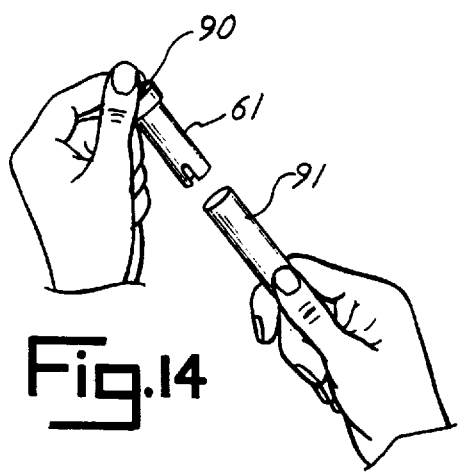
FIG. 14 illustrates the first step in the series of steps undertaken to utilize a guard construction of the invention.
Figure 15:
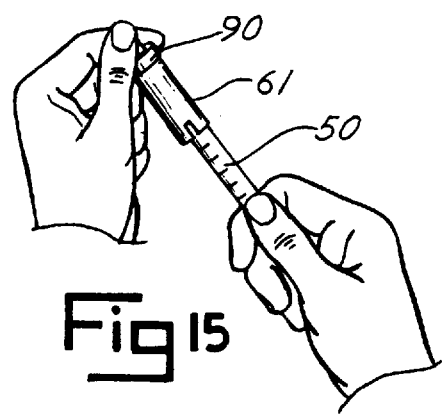
FIG. 15 illustrates the next sequential step.

When the needle guard 10 has been deformably affixed to the syringe barrel 25, the user removes the packaging cap 18, to expose the needle 43, now ready for use, as shown in FIG. 2C. After using the syringe and needle to inject a fluid into a patient, or to draw a sample of a fluid from a patient, the user grasps the sleeve 14 and pushes it axially forward, towards the needle 43, breaking the engagement between lips 42a, 42b and depressions 28a, 28b. The user slides the sleeve 14 until detent members 42a, 42b irreversibly engage slots 34a, 34b and shoulder 32 abuts bushing 16. The distal end of sleeve 14 now extends beyond the tip of contaminated needle 43, preventing any accidental injuries. The protected syringe may then be disposed of as a unit.

FIGS. 14 through 19 illustrate in greater detail the sequence of steps with respect to the use of the construction depicted in FIGS. I through 2D. Thus, initially, a protective assembly which is comprised of a sleeve 61, the fitting 60 within the sleeve 61, and a protective cap 90, are provided in combination with a disposable container 91. Container 91 fits over the open end of sleeve 61 to ensure sanitary conditions remain for the sleeve 61, fitting 60 and cap 90. The disposable container 91 is first manually removed from sleeve 61.

Figure 16:
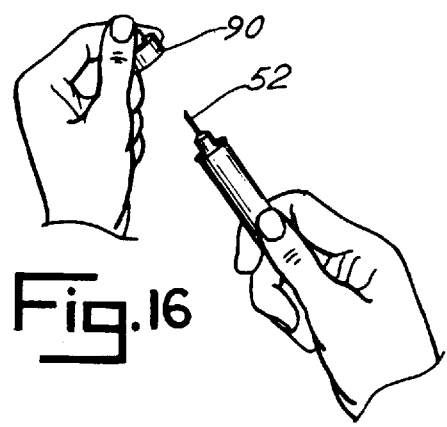
FIG. 16 illustrates a further sequential step; namely, the removal of the needle cap.

As the next step the syringe assembly including syringe body 50 is inserted into the sleeve 61. Since the needle 52 of the syringe assembly will fit into the disposable protective cap 90 there is a significantly reduced opportunity for the needle to stick the operator. The needle hub 53 is then inserted into and locked to the fitting 60, and the disposable protective cap 90 may then be removed as shown in FIG. 16. The assembly is then in the condition depicted in FIG. 16, as well as FIG. 2C. It will be noted that all of these operations can be performed without positioning the point of the needle 52 close to the nurse or doctor or other user. Additionally, when the disposable protective cap 90 is removed, such removal is accomplished by a motion of cap 90 away from the needle 52.

Figure 17:
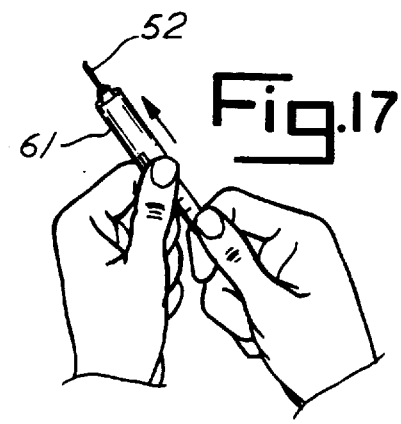
FIG. 17 illustrates the sequential step wherein the protective sleeve is longitudinally repositioned to cover the needle.
Figure 18:
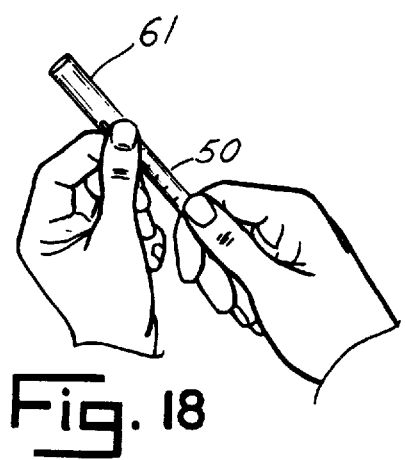
FIG. 18 depicts the next sequential step wherein the protective sleeve fully covers the needle.
Figure 19:
FIG. 19 illustrates the results of protected syringe assembly.

Next as shown in FIG. 17, the hypodermic assembly or syringe is used to administer a shot or for whatever purpose desired. Thereafter, the sleeve 61 is manually pushed forward to cover the needle 52, such as shown in FIG. 7 and depicted in FIGS. 18 and 19. Finally, the needle 52 and sleeve 61 may be removed from the hypodermic syringe assembly and all of the parts disposed of in a medically safe and sanitary manner.

As can now be seen, before, during and after use of the needle guard-syringe combination the user's hands are, at all times, kept a safe distance away from the needle 43. Before use, (during assembly) each of the user's hands is either safely behind the needle 43, or at a distance forward of the needle 43, separated by the length of the protective sleeve 14. During use of the syringe 12, the user's hands are again, either behind the needle 43, or grasping the sleeve 14 for support during injection/drawing. Finally, after use of the syringe 12, instead of placing a cap over the used syringe 12 and exposing the user to the danger of placing his or her hands near the contaminated needle 43, the user's hands remain safely behind the needle as the protective sleeve 14 is slid until it irreversibly extends beyond the tip of the needle, permanently preventing further access thereto.

As an alternative to providing the needle guard 10 as an "add on" product, the needle guard 10 may be provided already affixed to a syringe 13. In this embodiment, the needle guard 10 may be affixed to the syringe barrel 25 by mechanized means, as opposed to the manual method described above. The packaging cap 18 is not used during the mechanized assembly process. Instead, a machine containing a mold in the shape of the packaging cap 18 is used to supply the counter-force necessary to deformably engage the needle guard onto the syringe barrel 25 as described above. This pre-assembled embodiment may be more convenient for health care workers.

Turning now to FIGS. 3–7, there is illustrated a further or alternative embodiment of the invention. As shown in FIG. 3, a hypodermic syringe unit or assembly includes a syringe barrel 50, a separate needle assembly 51 including a hypodermic needle 52 retained in a needle hub 53, and a plunger (not shown) slidable in the syringe barrel 50 to effect injection or ejection of medicament or other material out of or into the syringe barrel 50. The hub 53 may comprise a luer lock element at its inner end as depicted. That is, hub 53 includes a locking flange 55 which cooperates with a groove 56 defined in the end of barrel 50 50 that the hub 53 may be twisted onto and into the syringe barrel 50 to be retained thereby. Note that the needle hub 53 includes a generally cylindrical forward section 57 with a series of longitudinal equally spaced ribs 58 on the outer circumference of the cylindrical section 57. The cylindrical section 57 then joins with a frusto-conical tapered section 59, which terminates with locking flange 55. The syringe assembly thus described constitutes a prior art syringe assembly which is compatible with the improved needle guard of the present invention, and in combination therewith comprises an aspect of the invention. The particular syringe assembly described and depicted is comprised of a removable hub 53 as contrasted with an integral hub 53 and barrel. However, the invention as described is useful with either a separable needle hub 53 or an integral needle hub of a syringe assembly or other needle device.

Continuing to refer to FIG. 3, the needle guard assembly for insertion onto the syringe assembly includes a fitting 60, a cooperative sleeve 61 and an optional needle cap or cover 230. The fitting or bushing 60 is positioned on the hub 53 and supports, in part, the sleeve 61 as discussed below and illustrated in more detail in FIG. 6. The needle cap or cover 230 may be frictionally fitted onto the end of the sleeve 61, again as depicted in FIG. 6.

FIGS. 4 and 5 illustrate in greater detail the construction of the bushing or fitting 60. Fitting 60 includes a central or core section 62 which has annular configuration. Thus core 62 includes a throughbore 63 with four (4) equally spaced slots 64 positioned about the inside periphery of the throughbore 63. The throughbore 63 has a generally uniform diameter. However the inner end of the throughbore 63 comprises a frusto-conical counter bore 65 as depicted in FIG. 5.

Generally radially extending flexible elastic arms 66 are connected to the core 62. The arms 66 are elastic and seek to maintain the diametrical configuration depicted in FIGS. 4 and 5. However, they may be biased inwardly to effectively reduce the diameter of the fitting 60. The arms 66 are thus elastic members which normally assume the configuration depicted. The end of each arm 66 terminates with a tang 67. The tangs 67 collectively define a maximum diameter for the fitting 60 which is slightly greater than the inside diameter of the sleeve 61. The reason for this will be apparent as explained below. Each of the tangs 67 includes a generally planar outer sliding surface 68 which is opposed to a slide surface in a compatible channel or slot 72 defined on the inside of sleeve 61. Longitudinal ribs 72a and 72b may be provided on one or both sides of each slot or channel 72. Each tang 67 also includes opposed, generally parallel surfaces 69 and 70 which define the width of the tang 67. The surfaces 69 and 70 are spaced to define a block which comprises the locking tab or tang 67 that coacts with the slots 72, and detents or recesses defined on the inside wall of the sleeve 61.

A preferred embodiment of the fitting is depicted in FIGS. 3 through 7 utilizing a "spiral" arm design, having four (4) equally spaced arms 66. In this spiral design, each elastic arm 66 is oriented such that the outer surface 68 of tang 67 on each arm 66 is at approximately a ninety degree angle to the surface where the core 62 meets the arm 66. This spiral design prevents the collapse of the arms 66, providing an improved locking mechanism.

FIGS. 6 and 7 illustrate, in greater detail, the construction of the sleeve 61 depicted in FIG. 3. The sleeve 61 is comprised of a clear plastic material molded in the form of a cylindrical barrel 71 with four equally spaced elongated tracks or slots 72 on the inside of the barrel 71. The slots 72 are generally parallel to the longitudinal axis 73 of the barrel 71. Each tang 67 is designed to slide in a separate slot 72 of the barrel 71. The barrel 71 includes a forward detent or rib 74 at the forward end of each slot 72. The rib or detent 74 serves to coact with the surface 69 and thereby retain the fitting 60 in a forward position in the barrel 71 as illustrated in FIG. 6. However, the arms 66, being elastic, will permit the tabs or tangs 67 to ride over the rib or detent 74 so that the barrel 71 can slide forward to the position as illustrated in FIG. 7. In the position illustrated in FIG. 7, the fitting 60 and more particularly the tangs 67 may fit into the openings 75 defined in the barrel 71 and located at the end or back side of each slot 72.

The barrel 71 also includes a larger diameter rear portion 76 with outwardly extending ribs 77. The ribs 77 are equally spaced about the periphery of the rear portion 76 of the barrel 71 and provide means for manual gripping of the barrel 71 for movement of the barrel 71 longitudinally. The ribs 77 may be serrated or shaped to facilitate gripping and movement.

The fitting 60, as previously described with respect to FIGS. 3, 4 and 5, receives the forward end of the hub 53. The radially projecting ribs 58 on the hub 53 slide into the slots 64 of the fitting 60. The core 62 is preferably molded from a material which is harder than the material used to manufacture the hub 53 though such a relationship is not necessary. In this manner, the fitting 60 can slide onto the hub 53 and more particularly, the front section 57 of the hub 53. The fitting 60 as aligned by the ribs 58, will frictionally engage, as well as partially deform the hub 53, particularly, the rear section 59 of the hub. This effectively locks the fitting 60 onto the needle hub 53 as illustrated in FIGS. 6 and 7. In the embodiment shown, the needle 52 is retained in a hub 53 which is designed to engage a luer lock 54 as previously described.

In practice then, the fitting 60 and cooperative sleeve 61 are fitted over the needle assembly 51 with the needle assembly 51 being attached to the syringe body 50 as depicted in FIG. 6. A plunger 80 for the syringe assembly is positioned in the desired position for either injection or withdrawal of fluids into the body 50 of the syringe assembly. The needle 52 projects through the forward end of the sleeve 61 and through the fitting 60 so that the nurse or doctor may utilize the hypodermic syringe in a desired fashion to inject medicament or to withdraw a fluid.

After manual operation of the plunger 80, the sleeve 61 may be manually pushed forward so as to slide over the fitting 60 permitting the tangs 67 to ride in the slots 72. At the end of each slot 72, each tang 67 is biased outwardly by a compressed arm 66 into the cooperative openings 75. The arms 66 are thus slightly biased when they ride in the slots 72 and tend to move outwardly upon movement in the openings 75. This insures that the tangs 67 will irreversibly lock into openings 75 when the sleeve 61 is moved to the forward or needle protective position as shown in FIG. 7. When the fitting 60 is in the position depicted in FIG. 7 with respect to the sleeve 61, the fitting 60 is irreversibly locked into that position. Since the fitting 60 is irreversibly locked, the needle 52, which is mounted on the hub 53, is also irreversibly locked into a protective position within the sleeve 61. The sleeve 61 may then be gripped, and, more appropriately, the ribs 77 may be manually gripped, and the sleeve 61 twisted to thereby detach the hub 53 from the luer lock 54. The sleeve 61 and the retained fitting 60, needle 52 and hub 53 may thus be disposed in a safe and sanitary fashion separate and apart from the syringe assembly. The potential for a needle-stick is thus eliminated by virtue of the fact that the sleeve 61 has been moved to enclose and protect the needle 52. Most importantly, the fitting 60 cooperatively engages the sleeve 61 to ensure that the needle 52 remains in a protected position.

Note that the hub 53 as described and depicted in FIG. 3 is removable from the syringe barrel 50, and therefore once the fitting 60 is engaged with hub 53, the hub 53, fitting 60 and sleeve 61 comprise a unitary assembly. That assembly may be retained on the syringe or removed as described. Alternatively, if the hub 53 is integral with the syringe, then the sleeve 61 remains fixed thereto to protect and cover the needle 52, and the entire syringe assembly may be disposed in a safe and sanitary fashion.

FIGS. 8 through 13 illustrate a further alternative construction for a sleeve 100 and bushing or fitting 110. Referring therefore to FIGS. 8 and 9, there is illustrated a sleeve 100 which is comprised of two component parts, namely a barrel 101 and a circular cap 102. The construction of the barrel 101 is similar to that of the sleeve 61 in FIG. 7, for example. Thus, there are channels or slots 103 and a forward detent 104 for cooperation with a tab or tang 119 associated with the fitting 110.

The cap 102, which is also illustrated in cross-section in FIG. 9, is a snap-on cap which may be snapped into position at one end of the barrel 101. Specifically, cap 102 includes a series of radial spaced, longitudinally extending arms 102a. Arms 102a interfit with complementary arms 101a of barrel 101. Arms 101a affix the cap 102 to the barrel 101. The arms 101a thus include circumferential ribs, e.g., ribs 101b, which lock with cooperating ribs or grooves, e.g., grooves 102b. The inside surface of each arm 102a also defines an extension of the channels or slots 103 and further include the projections or detents 104 which co-act with fitting 110.

The cap 102 also includes a throughbore passage 106 which is designed to receive the needle 52. The cap 102 has a generally frusto-conical shape and includes a forward rib 107 andgroove 108 which are designed to cooperatively engage with a compatible, elongated protective cap (not shown), analogous to cap 62 in FIG. 3, which fits over needle 52 projecting through the throughbore 106. FIG. 10 is a cross-sectional view illustrating the components parts in their assembled conditioned as shown in FIGS. 8 and 9.

The alternative two-part design of the sleeve 100 in FIG. 8, may be easier to mold than the single unit design of the sleeve 61 in FIG. 3. The cap 102 acts to eliminate foreign objects, including a user's fingers from entering the sleeve 100.

FIGS. 11, 12 and 13 illustrate the alternative construction for the fitting 110 that may be used with sleeve 100. Referring to these figures, fitting 110 includes a core III which is a generally annular member having a throughbore 112 with equally spaced longitudinal slots 113 about a centerline axis 114 of the throughbore 112. The throughbore 112 terminates with a frusto conical bore section 115, as shown in FIG. 13.

A first set of four (4), equally sized and uniformly spaced radial arms 116 project in a fan-like fashion from the core 111 and define a generally planar element extending from the core 111. The arms 116 include a inclined outer surface 117. The arms 116 are elastic members which are flexible, but generally snap back to the position shown in FIG. 13. The arms 116 are spaced axially from a second set of four (4) equally sized and uniformly spaced arms 118 which also extend radially from the core 111 and arc axially forward of the arms 116 in the direction of needle 52. The arms 116 and 118 are circumferentially alternating. In the embodiment depicted, there are four arms 118. Each arm 118 terminates with a tang 119 which is designed to slidably fit into slot 103 to thereby guide the sleeve 100 over the fitting 110.

FIGS. 20, 21 and 22 illustrate a further alternative construction for the fitting 210 that may be used with sleeve 100. Referring to these figures, fitting 210 includes a core 211 which is a generally annular member having throughbore 212 with equally spaced longitudinal slots 213 about a centerline axis 214 of the throughbore 212.

A first set of four (4) equally sized and uniformly spaced radial arms 216 project in a fan-like fashion from the core 211. The arms 216 include inclined outer surface 217. The arms define elastic members which are flexible, but generally snap back to the position shown in FIG. 21.

A second set of four (4) equally sized and uniformly spaced radial arms 218 also project in a fan-like fashion from the core 211 and are axially forward of the arms 216 in the direction of needle 52. Each arm 218 terminates with a tang 219 which is designed to slidably fit into slot 103 to thereby guide the sleeve 100 over the fitting 210. The arms 216 and 218 are circumferentially alternating. In contrast to the fitting 110 of FIGS. 11–13, the two sets of arms of fitting 210 are not spaced axially from each other, but instead are molded integrally with each other. This integrally molded design causes the arms to be more axially rigid than the design of fitting 110, to thereby improve the irreversible locking mechanism, described below.

Fitting 210 also contains a first set of four (4) radial support ribs 221, located on the core 211. Support ribs 221 further add to the axial rigidity of arms 218. Support ribs 221 are equally sized and uniformly spaced about core 211. A second set of four (4) radial support ribs 220 are also located on core 211. Support ribs 220 are equally sized and uniformly spaced about core 211, intermediate radial support ribs 221. Support ribs 220 lend axial rigidity to arms 216. Further, support ribs 220 are formed in generally a right angle planar surface, allowing ribs 220 to coact with cap 102 to prevent the fitting from rotating when placed within cap 102.

Referring to FIG. 10, two sets of inwardly projecting ribs 120 and 122 comprise a locking means for the needle guard. Upper ribs 120 are distributed about the interior of sleeve 100 in four sets, having two or three ribs per set. Upper ribs 120 are oriented about the sleeve 100 so as to coact with flexible arms 216.

Lower ribs 122 are also distributed about the interior of sleeve 100 in four sets, having two or three ribs per set. Lower ribs 122 are oriented about the sleeve 100 so as to coact with flexible arms 218.

On the surface of upper ribs 120 facing the direction of the needle 52, ribs 120 take the shape of inclined planes sloping downwardly in the direction of the needle 52. The face on upper ribs 120 opposite the inclined plane is at approximately a right angle to the interior surface of sleeve 100.

On the surface of lower ribs 122 facing the direction of the needle, ribs 122 are at approximately right angles to the interior surface of sleeve 100. The opposite face of lower ribs 122 may be in the shape of inclined planes, sloping downwardly in the direction opposite the needle 52.

In the fitting 210 of FIG. 20, arms 216 are located intermediate each of the arms 218. The arms 216 are designed to cooperatively engage with upper ribs 120 on the inside of the sleeve 100 to thereby irreversibly lock the sleeve in a position which protects a needle 52. That is, when the sleeve 100 is moved to the protected position covering needle 52, the inclined surface 217 of arms 216 will cause the arms 216 to ride over the inclined surface of upper ribs 120 and to become locked behind the right angle surface of upper ribs 120. When arms 216 reach this locked position, arms 218 will be abut the right angle surface of lower ribs 122, thus preventing further axial movement. The arms of the fitting and ribs of the sleeve will thus be positioned so that sleeve 100 becomes tightly and irreversibly locked in position so that the sleeve 100 covers the needle 52.

Referring to FIG. 8, inwardly projecting ridge 121 comprises an alternative locking means that may be used with the fitting 110. Ridge 121 is a generally annular continuous circumferential ring about the internal surface of sleeve 100.

The face of ridge 121 facing the needle 52 slopes downwardly in the direction of the needle 52. The face of ridge 121 opposite the needle 52 is at generally a right angle to the interior surface of sleeve 100.

The arms 116 of fitting 110 are designed to cooperatively engage with inwardly projecting ridge 121 on the inside of the sleeve 100 to thereby lock the sleeve 100 in a position which covers or protects a needle 52. That is, the inclined surface 117 of arms 116 will cause the flexible arms 116 to ride over the inclined face of ridge 120 and to become locked behind that ridge 120 upon movement of sleeve 100 over needle 52. Arms 118, not having an inclined surface, will not ride over ridge or ribs 120, but instead will abut them. The ridge 120 will thus be positioned in between or in the space defined by the axially spaced set of arms 116 and the arms 118. In this manner, the sleeve 100 becomes tightly and irreversibly locked in position so that the sleeve 100 covers the needle 52.

Thus, in review, in use, the spiral or SPYDER™ fitting of FIGS. 3 through 7 may be secured to the needle hub through the deformable and frictional attachment process described above. The fitting-needle hub combination is then joined to the syringe barrel, and the entire assembly is then placed within the protective sleeve. This assembly in most instances will be accomplished by a machine. The embodiments utilizing the alternative SPYDER™fittings 110 and 210, as shown in FIGS. 11 through 13, and 20 through 22, respectively as well as the sleeve 100 shown in FIGS. 8 through 10, are also expected to come pre-assembled by machine for the health-care worker's convenience the needle manufacturer attaches the bushing on the needle hub through the deformable and frictional attachment process described above in FIGS. 3 through 7. The needle is then attached to the needle hub. The bushing-needle combination is then be inserted into the cap, the sleeve secured to that assembly, and finally the syringe barrel is inserted into the needle hub. A similar sequence of steps would be used for a syringe having a permanently mounted needle.

Although exemplary embodiments of the invention have been shown and described, many changes and substitutions may be made by one of ordinary skill in the art without departing from the scope of this invention. For example, the needle hub and fitting may be molded as a unitary integral unit. Furthermore, although the sleeve 61 is disclosed to be fully or partially translucent, it may be readily seen that the sleeve could be made of opaque materials except for a window or slot which allows the measure of the syringe to be read. In other applications, where it is not necessary to read a direct measurement off a syringe barrel, the shield may be completely opaque. This invention is suited for use with any medical or industrial instrument, such as intravenous needles or catheters, or other instruments which have a sharp point or blade. Other versions of this needle guard may be adapted for use with other types of syringes and medical implements without departing from the scope of this invention. The construction of the fittings 60 and 110 may also be varied. This invention therefore includes alternatives to the specific configurations described in the exemplary embodiments and is limited only to the language of the claims and equivalents thereof.

What is claimed is:

1. A needle guard for a hypodermic syringe assembly having a syringe barrel and a hypodermic needle mounted on a needle hub that is attachable on and detachable from said syringe barrel, said needle guard comprising a separate guard assembly which is attachable to said syringe assembly and which in combination therewith maintains either a non-protective or an irreversible protective configuration with respect to said needle, said needle guard comprising:

a separate attachable fitting having an annular core and a plurality of radially extending elastic arms ending in a tang, said arms extending from said core having an interior portion with deformable engagement means for cooperatively mounting said fitting in a fixed position on said needle hub by penetrating the surface of said needle hub;

a hollow protective sleeve having an interior surface, an exterior surface, a distal end, a proximal end, and a guide means for slidably connecting said interior surface of said sleeve with said arms of said fitting, said sleeve thereby being movable on said fitting axially in the direction of the length of said needle between a non-protective retracted position exposing said needle and a protective, extended position covering said needle; and means for irreversibly locking said sleeve only in said protective, extended position relative to said fitting, whereby axial and rotational movement of said sleeve relative to said fitting is prevented, and whereby said sleeve in said protective, extended position protrudes beyond the tip of said needle such that said sleeve defines a guard which irreversibly prevents further access to said needle once said sleeve has been moved to said extended position, wherein said needle guard, said needle, and said needle hub are removable as one unit from said syringe barrel by detachment of said needle hub from said barrel when said sleeve is in said protective, extended position and is irreversibly locked.

2. A method for guarding a user of a hypodermic syringe from a needle stick during use of said syringe, said syringe having a syringe barrel and a hypodermic needle mounted on a needle hub that is attachable on and detachable from said syringe barrel, said method comprising the steps of:

inserting a fitting, that is separate from said needle and said needle hub, into a protective sleeve to form a fitting-sleeve assembly, said fitting being adapted to retain said sleeve on said fitting;

preventing temporarily axial movement of said fitting relative to said sleeve;

mounting said hypodermic syringe into said fitting-sleeve assembly by directing said syringe into said protective sleeve;

causing the interior surface of the fitting to penetrate the surface of said needle hub by applying an axial force to said syringe in the direction of said needle, while simultaneously supplying an axial counter-force to said fitting which cooperatively mounts in a fixed position on said needle hub;

using said hypodermic syringe by forcing fluid through said needle while said sleeve is retained in a non-protective retracted position exposing said needle;

sliding said protective sleeve in the direction of said needle relative to said barrel such that said sleeve extends beyond the tip of said needle in a protective, extended position after said step of forcing fluid through said needle; and removing said fitting-sleeve assembly, said needle, and said needle hub, as one unit, from said syringe barrel by detachment of said needle hub from said barrel when said sleeve is in said protective, extended position.

3. A method for guarding a user of a hypodermic syringe from a needle stick during use of said syringe, said syringe having a syringe barrel and a hypodermic needle mounted on a needle hub that is attachable on and detachable from said syringe barrel, said method comprising the steps of:

inserting a fitting, that is separate from said needle and said needle hub, into a protective sleeve to form a fitting-sleeve assembly, said fitting being adapted to retain said sleeve on said fitting;

preventing temporarily axial movement of said fitting relative to said sleeve;

mounting said hypodermic syringe into said fitting-sleeve assembly by directing said syringe into said protective sleeve;

causing the interior surface of the fitting to penetrate the surface of said needle hub by applying an axial force to said syringe in the direction of said needle, while simultaneously supplying an axial counter-force to said fitting which cooperatively mounts in a fixed position on said needle hub;

using said hypodermic syringe by forcing fluid through said needle while said sleeve is retained in a non-protective retracted position exposing said needle;

sliding said protective sleeve in the direction of said needle relative to said barrel such that said sleeve extends beyond the tip of said needle in a protective, extended position after said step of forcing fluid through said needle; and irreversibly locking said protective sleeve beyond the tip of said needle when said sleeve is in said protective, extended position.

4. The method of claim 3, further including the step of:

removing said fitting-sleeve assembly, said needle, and said needle hub, as one unit, from said syringe barrel by detachment of said needle hub from said barrel when said sleeve is irreversibly locked and is in said protective, extended position.

5. A method for guarding a user of a medical instrument from a needle stick during use of said instrument, said instrument having a barrel for carrying fluid and a needle for injecting said fluid, said needle mounted on a needle hub that is attachable on and detachable from said barrel, said method comprising the steps of:

inserting a fitting, that is separate from said needle and said needle hub, into a protective sleeve to form a fitting-sleeve assembly, said fitting being adapted to retain said sleeve on said fitting;

preventing temporarily axial movement of said fitting relative to said sleeve;

mounting said instrument into said fitting-sleeve assembly by directing said instrument into said protective sleeve;

causing the interior surface of the fitting to penetrate the surface of said needle hub by applying an axial force to said syringe in the direction of said needle, while simultaneously supplying an axial counter-force to said fitting which cooperatively mounts in a fixed position on said needle hub;

using said instrument by forcing fluid through said needle while said sleeve is retained in a non-protective retracted position exposing said needle;

sliding said protective sleeve in the direction of said needle relative to said barrel such that said sleeve extends beyond the tip of said needle in a protective, extended position after said step of forcing fluid through said needle; and removing said fitting-sleeve assembly, said needle, and said needle hub, as one unit, from said barrel by detachment of said needle hub from said barrel when said sleeve is in said protective, extended position.

6. A method for guarding a user of a medical instrument from a needle stick during use of said instrument, said instrument having a barrel for carrying fluid and a needle for injecting said fluid, said needle mounted on a needle hub that is attachable on and detachable from said barrel, said method comprising the steps of:

inserting a fitting, that is separate from said needle and said needle hub, into a protective sleeve to form a fitting-sleeve assembly, said fitting being adapted to retain said sleeve on said fitting;

preventing temporarily axial movement of said fitting relative to said sleeve;

mounting said instrument into said fitting-sleeve assembly by directing said instrument into said protective sleeve;

causing the interior surface of the fitting to penetrate the surface of said needle hub by applying an axial force to said syringe in the direction of said needle, while simultaneously supplying an axial counter-force to said fitting which cooperatively mounts in a fixed position on said needle hub;

using said instrument by forcing fluid through said needle while said sleeve is retained in a non-protective retracted position exposing said needle;

sliding said protective sleeve in the direction of said needle relative to said barrel such that said sleeve extends beyond the tip of said needle in a protective, extended position after said step of forcing fluid through said needle; and irreversibly locking said protective sleeve beyond the tip of said needle when said sleeve is in said protective, extended position.

7. The method of claim 6, further including the step of:

removing said fitting-sleeve assembly, said needle, and said needle hub, as one unit, from said barrel by detachment of said needle hub from said barrel when said sleeve is irreversibly locked and is in said protective, extended position.

8. A needle guard for a hypodermic syringe assembly including a hypodermic needle and a syringe barrel having a lead portion adjacent the hypodermic needle, the needle guard comprising a separate assembly which is attachable to the syringe assembly and which in combination therewith maintains either a nonprotective or a protective configuration for the needle, said needle guard comprising in combination:

a separate attachable fitting having an exterior portion and an interior portion, the interior portion being adapted to cooperatively mount in a fixed position on the lead portion of the barrel by frictionally, removably engaging the lead portion of the barrel;

a hollow, protective sleeve on the fitting, said sleeve having an interior surface adapted to coact with the fitting, and exterior surface, a distal end and a proximal end;

guide means for slidably connecting the interior surface of said sleeve and the exterior portion of said fitting, said sleeve thereby being movable on the fitting axially in the direction of the length of the needle between a non-protective retracted position exposing the needle and a protective, extended position covering the needle; and means for retaining said sleeve in the protective, extended position covering the needle, said means for retaining being comprised of at least one member located on the exterior surface of the fitting extending from the fitting, and an outwardly extending lip extending from the member, the lip being biased radially outward to engage the sleeve, and the sleeve being adapted to engage the lip in the extended position.

9. The needle guard of claim 8 wherein the retaining means comprises means for irreversible locking engagement of the sleeve and fitting in the extended position.

10. The needle guard of claim 8 wherein the tang is biased radially outward by the rib.

11. The needle guard of claim 8 wherein the at least one elastic cantilevered rib located on the exterior surface of the fitting extends radially from the fitting.

12. A needle guard for a hypodermic syringe assembly including a hypodermic needle and a barrel having a lead portion adjacent the hypodermic needle, the needle guard comprising an assembly which is attachable to the barrel and which in combination therewith maintains either a non-protective or a protective configuration for the needle, said needle guard comprising in combination:

a fitting having an exterior portion and an interior portion, the interior portion being adapted to cooperatively mount in a fixed position on the lead portion of the barrel by frictionally, removably engaging the lead portion of the barrel;

a hollow, protective sleeve on the fitting, said sleeve having an interior surface and an exterior surface;

an outwardly extending tang extending axially from the fitting in the direction of the needle and biased radially outward to engage the sleeve;

the sleeve adapted to engage the tang and retain the sleeve in a protective extended position covering the needle.

13. The needle guard of claim 12 wherein the interior surface of the sleeve includes at least one detent that engages the tang and locks the sleeve in the protective extended position covering the needle.

\* \* \* \* \*